United States Patent [19]
Heck et al.

[11] Patent Number: 5,792,151
[45] Date of Patent: Aug. 11, 1998

[54] METHOD AND APPARATUS FOR LIGATING A BLOOD VESSEL, TISSUE OR OTHER BODILY DUCT

[75] Inventors: Christopher F. Heck; Eric R. Schertel, both of Columbus, Ohio; William H. Strater, High Point, N.C.

[73] Assignee: The Ohio State University, Columbus, Ohio

[21] Appl. No.: 590,786

[22] Filed: Jan. 24, 1996

[51] Int. Cl.⁶ .................................................. A61B 17/04
[52] U.S. Cl. .......................... 606/144; 606/139; 606/145; 606/148; 112/169
[58] Field of Search .................... 606/139, 144, 606/145, 148; 112/169, 80.03

[56] References Cited

U.S. PATENT DOCUMENTS

| | | |
|---|---|---|
| 4,349,028 | 9/1982 | Green. |
| 4,556,058 | 12/1985 | Green. |
| 4,608,428 | 8/1986 | Shalaby et al.. |
| 4,641,652 | 2/1987 | Hutterer et al.. |
| 4,935,027 | 6/1990 | Yoon ............................ 606/148 |
| 4,957,498 | 9/1990 | Caspari et al.. |
| 4,961,741 | 10/1990 | Hayhurst. |
| 5,037,433 | 8/1991 | Wilk et al. ..................... 606/144 |
| 5,074,874 | 12/1991 | Yoon et al.. |
| 5,078,721 | 1/1992 | McKeating. |
| 5,087,263 | 2/1992 | Li. |
| 5,098,137 | 3/1992 | Wardall. |
| 5,181,919 | 1/1993 | Bergman et al.. |
| 5,192,287 | 3/1993 | Fournier et al.. |
| 5,234,443 | 8/1993 | Phan et al.. |
| 5,242,459 | 9/1993 | Buelna ........................... 606/148 |
| 5,250,054 | 10/1993 | Li. |
| 5,261,917 | 11/1993 | Hasson et al.. |
| 5,281,236 | 1/1994 | Bagnato et al.. |
| 5,306,280 | 4/1994 | Bregen et al.. |
| 5,312,423 | 5/1994 | Rosenbluth et al.. |
| 5,312,642 | 5/1994 | Chesterfield et al.. |
| 5,324,307 | 6/1994 | Jarrett et al.. |
| 5,336,229 | 8/1994 | Noda. |
| 5,336,231 | 8/1994 | Adair .............................. 606/148 |
| 5,470,338 | 11/1995 | Whitfield. |
| 5,472,446 | 12/1995 | de la Torre ..................... 606/148 |
| 5,501,683 | 3/1996 | Trott. |

FOREIGN PATENT DOCUMENTS

| | | |
|---|---|---|
| 2103092 | 11/1993 | Canada. |
| 2600880 | 3/1986 | France. |
| 42 102 55 | 4/1993 | Germany. |
| WO 94/05217 | 3/1994 | WIPO. |
| WO 94/05220 | 3/1994 | WIPO. |

OTHER PUBLICATIONS

Insurg Boston Scientific Corporation *When It's Time to Tie the Knot* Sep. 1994.

*Primary Examiner*—Gary Jackson
*Attorney, Agent, or Firm*—Calfee, Halter & Griswold LLP

[57] ABSTRACT

A reusable ligation apparatus includes a suture tying or knot tying instrument and a suture cartridge containing a preformed ligature. The cartridge is releasably attached to the instrument so that after a first ligature is made, the apparatus enables one-handed ligation, and can be quickly reloaded with a second cartridge for making another ligature without delay. The cartridge contains a preformed ligature and the instrument includes an activation system which automatically pulls one end of the preformed ligature through loops formed in the other end to thereby form a completed ligature knot.

35 Claims, 13 Drawing Sheets

METHOD AND APPARATUS FOR LIGATING A BLOOD VESSEL, TISSUE OR OTHER BODILY DUCT

FIELD OF THE INVENTION

This invention relates generally to the field of surgical instruments and methods. More particularly, it relates to a ligation device, or a suture tying or knot tying device, for automatically ligating tissue or a bodily duct with a preloaded length of suture material.

BACKGROUND OF THE INVENTION

One of the more time-consuming and difficult surgical tasks to perform with precision is the tying-off or ligation of blood vessels, tissue or ducts that connect two organs. Typically, the surgeon must use both hands to perform the multiple steps required for forming and tightening the knot. In addition, the surgeon must consistently and precisely form a knot which remains tight for an extended period of time and during movement by the patient.

Proper ligation requires even more dexterity and time during laprascopic surgery. In laparoscopy, all of the surgical procedures, including ligating, are performed by means of elongated instruments that are inserted through small, minimally invasive incisions or punctures. Thus, ligation during laparoscopic surgery requires the passing of sutures and the tying of knots remotely, using elongated forceps under videoscopic observation.

In this regard, it is desirable for a ligature forming device to remotely perform the function of knot-tying. It is also desirable to provide a ligature forming device that relieves the surgeon of intricate knot-tying maneuvers and the multiple steps required to perform the procedure. To further facilitate ligature forming, it is desirable to provide a self-contained ligature forming device reducing the number of instruments involved in the procedure.

To minimize the time and skill required to ligate blood vessels, tissue and ducts during laparoscopic surgery several devices utilizing clips rather than sutures have been developed. However, clips are prone to dislogdement. In addition, clips either remain as foreign bodies in the patient or must be removed during a second procedure. In contrast, sutures can be formed with material that dissolves in the patient.

Typically the use of sutures involves manual preparation of the sutures before ligating. This manual preparation includes the formation loops, tag ends and knots in the suture material requiring considerable time and dexterity. Once prepared the suture material must then be strung through and around the ligature instrument. This is very time consuming and hence very disadvantageous during surgery where it is important to finish as quickly as possible.

While a number of prior art suture-tying devices have been developed for ligating blood vessels or ducts, each has shortcomings. For example, some suture-tying devices require the surgeon to learn complicated new knots. Others require additional instruments and/or additional access sites to complete or tighten the knot. Some devices use preformed loops that can only be applied to the cut ends of a blood vessel or duct and, thus, necessitate division of the vessel or duct. The preformed loops on these devices also have a tendency to lock prematurely, that is, before the ligature is finally cinched in place.

U.S. Pat. No. 5,312,423 to Rosenbluth et al. discloses a device for laprascopic ligation of blood vessels that has an elongated tube with an attached finger for grasping and isolating the blood vessel or duct and for holding a tag end of suture material its tip. While the Rosenbluth device does not require the surgeon to manually tie the knot, it does require several manipulations by the surgeon at the point of ligation. For example, in addition to activating the rod which snags the suture material, the surgeon must perform several different manipulations to withdraw the mandrel into the handle. The surgeon must also perform additional manipulations of the instrument to cut the suture material. In addition to being time-consuming, these manipulations require the surgeon to use both hands.

Moreover, the surgeon must either discard the entire Rosenbluth device after a single use of have his or her assistant re-load the suture material which requires considerable skill and time. Another potential drawback with the Rosenbluth device is the possibility of injury to the tissue surrounding the blood vessel during operation of the device. Such injury could occur when the hooked end of the rod is extended beyond the mechanical finger which holds the blood vessel or when surrounding tissue comes into contact with the exposed cutting blade during the cutting manipulations.

Thus, there is a need for an improved ligation device that requires few manipulations by the surgeon to ligate a blood vessel, duct or other tissue and that poses less of a threat of injury to the tissues surrounding the blood vessel during operation. There is also a need for an improved ligation device to be reusable with minimal manipulations and time required to reload and restring the device.

SUMMARY OF THE INVENTION

The present device provides a ligation device for automatically ligating a blood vessel, tissue or duct with a length of suture material. In particular, the device enables the surgeon to accomplish the ligation using one hand. The device includes a cartridge releasably attached thereto.

The cartridge, which is configured to isolate and receive a vessel, tissue or duct, contains a preformed ligature therein. The device or instrument in turn, includes an activation system which automatically pulls one end of the preformed ligature through loops formed in the other end to thereby form a loose, but completed, ligature knot. In a preferred embodiment, the instrument is adapted to pull both ends of the loosely-formed ligature knot tight, thereby forming a completed knot. The instrument can then be removed from its use location, the spent cartridge replaced with a fresh cartridge, and the apparatus immediately used again for completing a second ligature.

BRIEF DESCRIPTION OF THE DRAWINGS

The present invention may be more readily understood by reference to the drawings wherein.

DETAILED DESCRIPTION

Figure 1A:
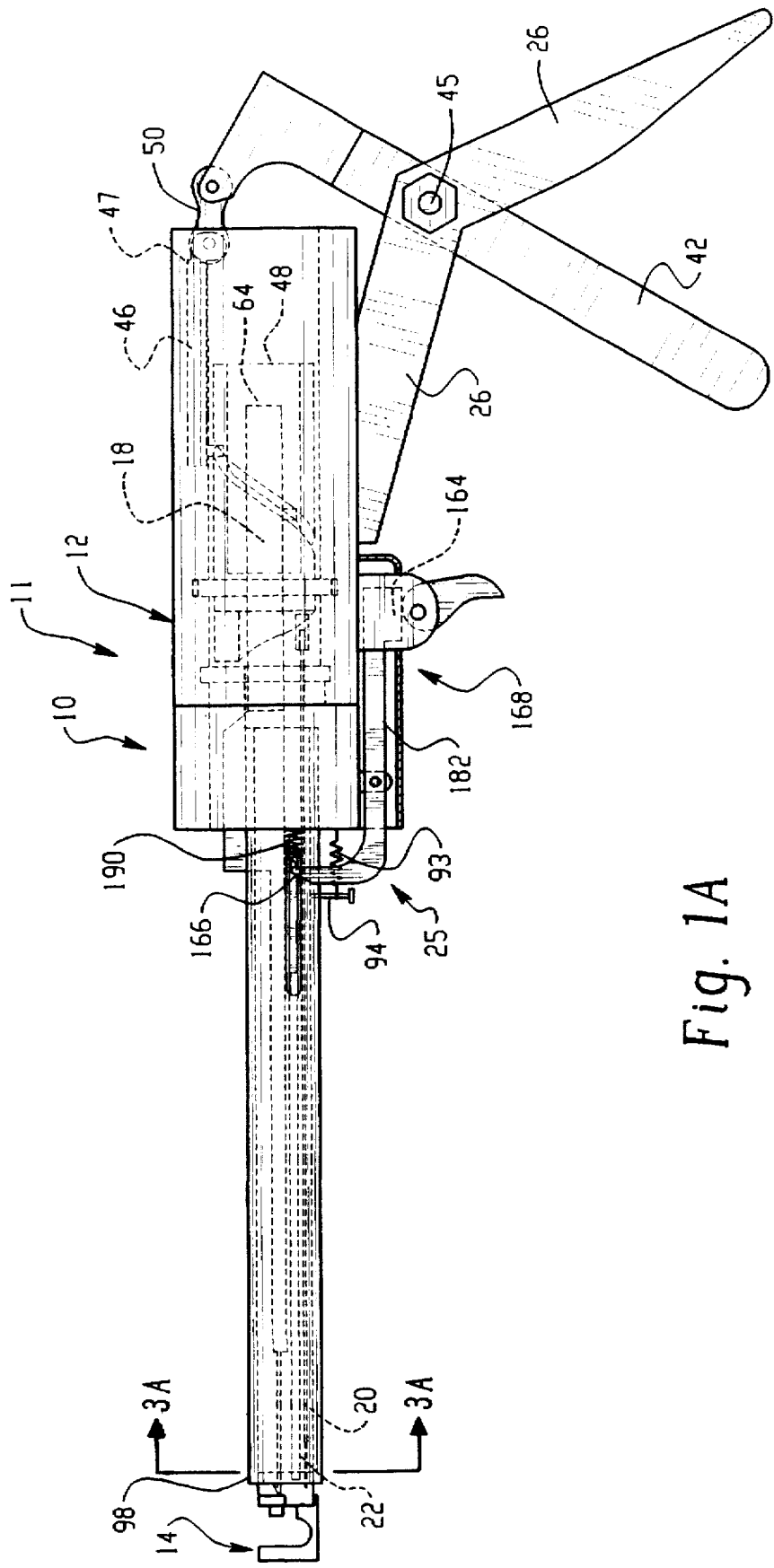
FIG. 1A illustrates a preferred embodiment of a ligation apparatus constructed in accordance with the present invention including an instrument and a ligature-containing cartridge.
Figure 1B:
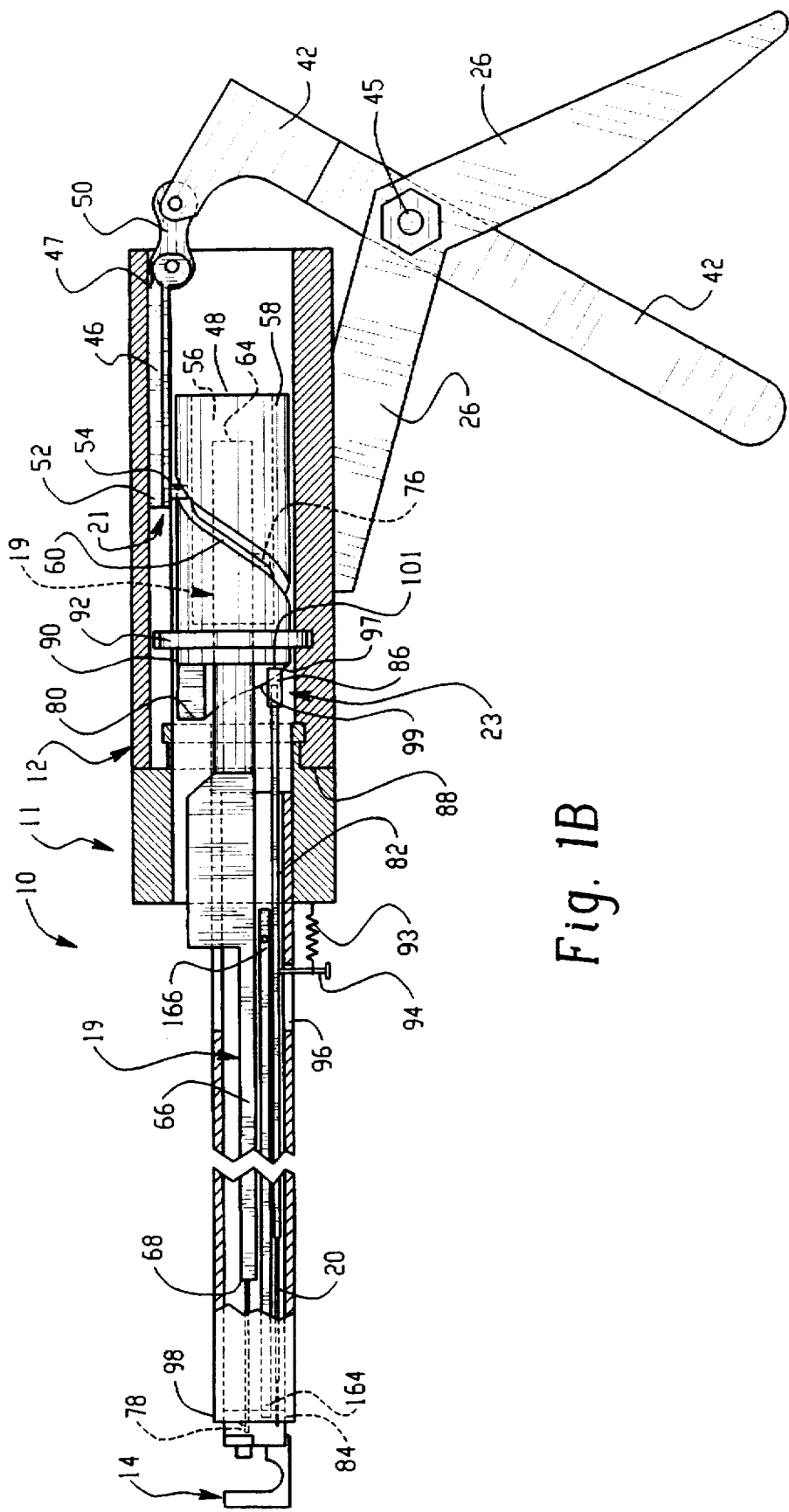
FIG. 1B is a fragmentary, axial, cross-sectional view of the ligation apparatus of FIG. 1A.

Referring to FIGS. 1A and 1B, the inventive ligation apparatus 10 includes an instrument 11 and a holding member or cartridge 14. Cartridge 14 in turn is composed of a cartridge blank and a preformed ligature preloaded in the cartridge blank. For ease of explanation, a number of the drawings herein do not show the preformed ligature in place in the cartridge. However, it will be understood that the cartridge as is typically obtained from the manufacturer, or as preloaded by the user, will contain a preformed ligature therein.

Figure 13A:
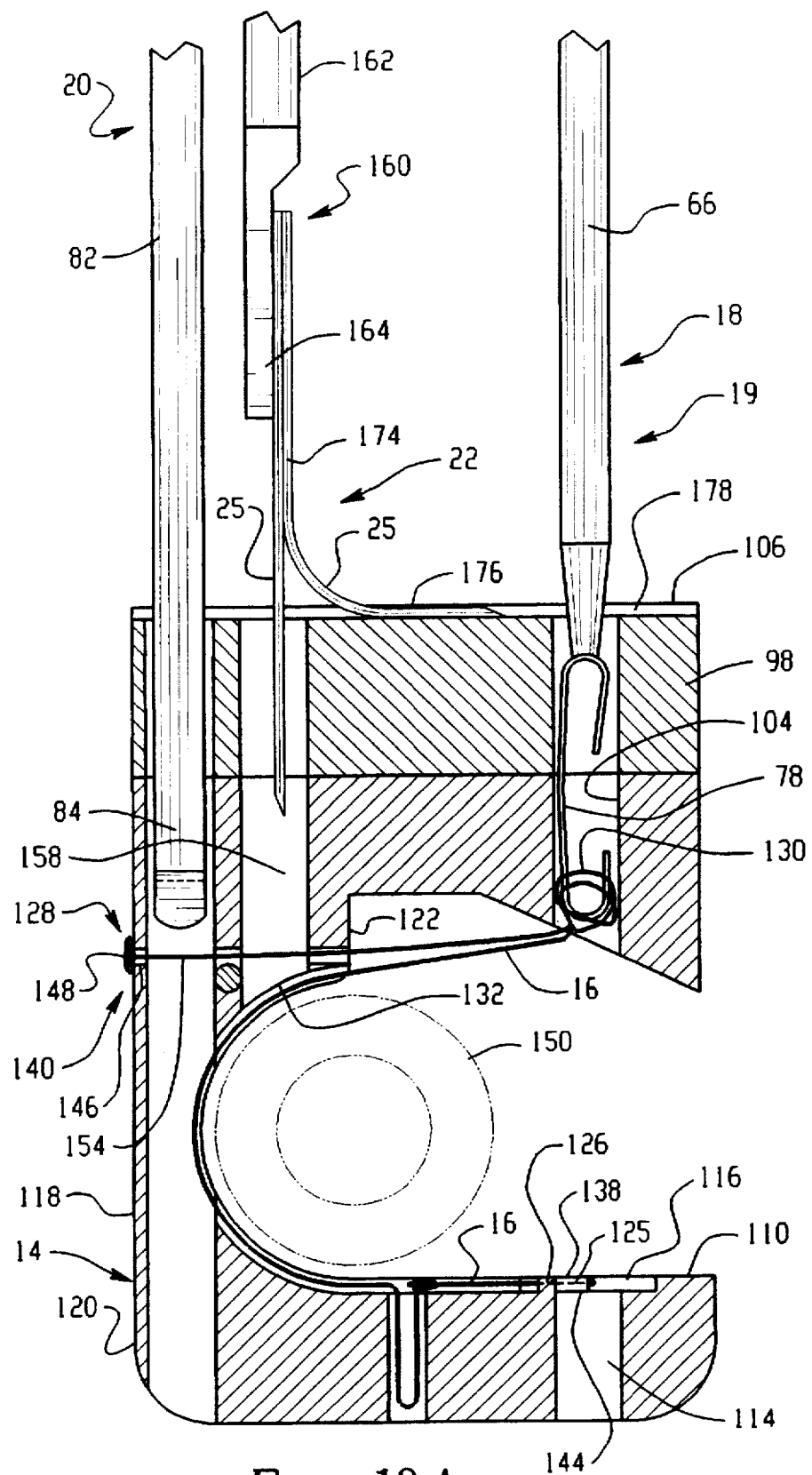
FIG. 13A is a fragmentary cross-sectional view of a front portion of the inventive ligation apparatus showing the front of the surgical knot-tying instrument of FIGS. 1A and 1B being attached to the cartridge of FIG. 6, with the apparatus being in an initial configuration ready for use in automatically forming a ligature.

Cartridge 14 is removably attached to a front end 98 of elongated frame or body 12 of the instrument 11. As seen in FIGS. 1A, 1B and 13A, the instrument 11 includes a number of assemblies for performing various operations on the suture material 16 contained in cartridge 14. Specifically, instrument 11 includes: (i) capture means 18 for moving the suture material around the vessel to form a knot wherein capture means 18 comprise a capture member or hook assembly 19 and a drive assembly 21, (ii) tightening means 20 for tightening the knot including a push assembly 23 and a tightening member 82, (iii) and cutting means 22 for cutting the suture material after formation of the knot including a cut assembly 25.

For operating ligation apparatus 10, surgical knot-tying instrument 11 includes a handle 26 and an actuator 42 pivotally mounted on handle 26 by a conventional connector 45. Actuator 42 is attached to drive assembly 21 which includes an outer link bar 46 and an outer cylindrical drive cam 48 rotatably positioned within instrument 11. Link bar 46 has a first end 47 connected to actuator 42 via connecting mechanism or handle link 50.

Figure 2:
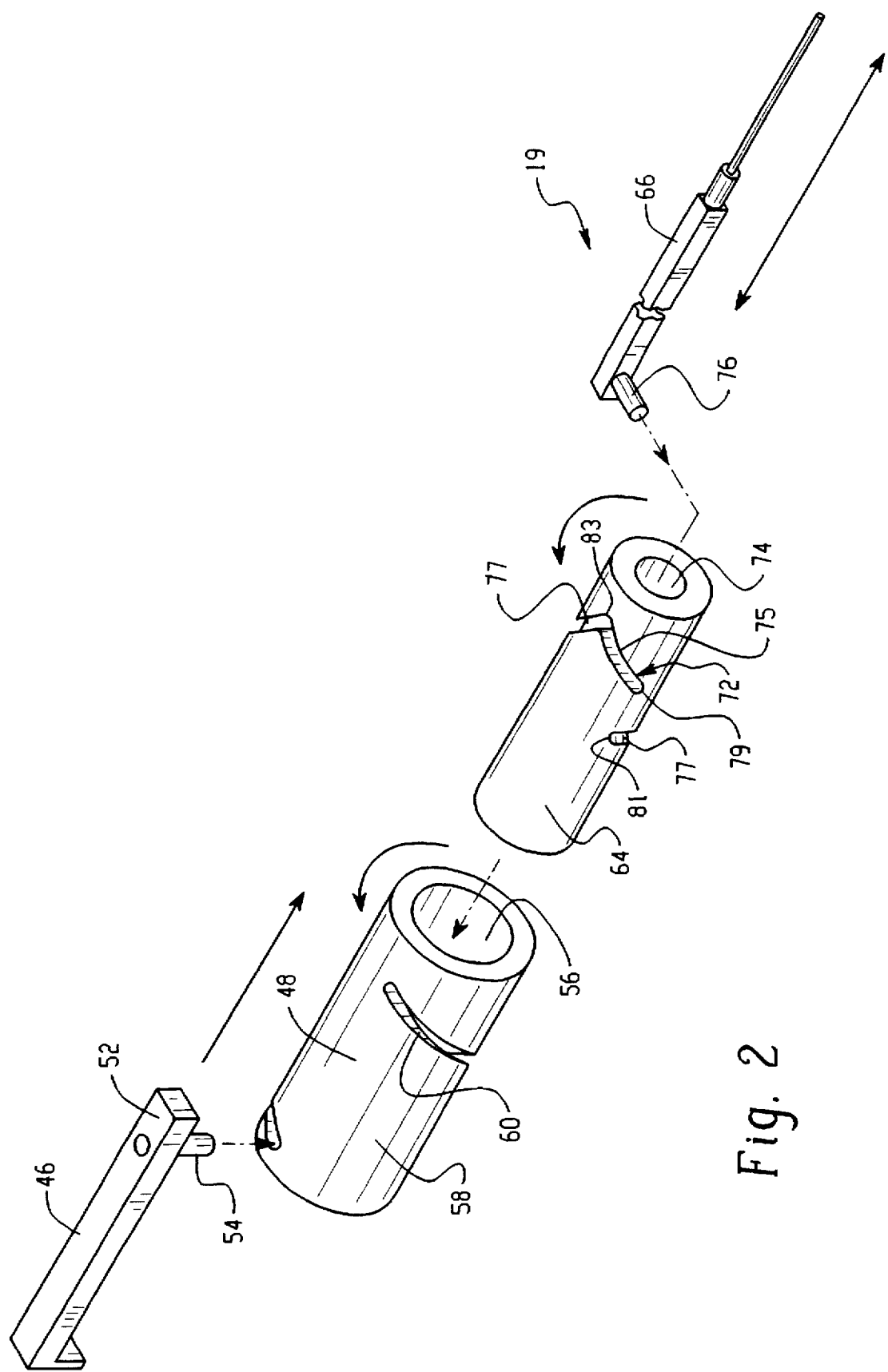
FIG. 2 is an exploded perspective view of a portion of the driving mechanism used to actuate the grasping and tightening members of the instrument of the inventive apparatus.

Referring to FIGS. 1B and 2, a second end 52 of link bar 46 includes an outer cam pin 54 extending therefrom. Outer drive cam 48 has a generally cylindrical configuration with an inner cylindrical opening 56 and an outer cylindrical surface 58. A helical outer drive cam groove 60 is located in outer surface 58 for receiving outer cam pin 54 of link bar 46. Upon movement of actuator 42 towards handle 26, link bar 46 is moved axially forward causing outer cam pin 54 to move within outer groove 60 and thereby rotate outer drive cam 48 in a clockwise direction as viewed from the rear of the instrument.

As shown in FIG. 2, a hollow cylindrical inner drive cam 64 is positioned within, and integrally secured to, outer drive cam 48. An inner drive cam groove 72 is located in the inner surface 74 of inner cam 64. The continuous inner cam groove 72 is composed of two interconnected grooved legs which are directionally discrete; a forward groove leg 75 extending circumferentially approximately 90° around inner cylindrical surface 74 of inner drive cam 64 and a rearward groove leg 77 extending circumferentially about 270° around inner cylindrical surface 74. Both groove legs 75 and 77 are helical in configuration and are connected at a junction 83 located at the forwardmost axial position of groove 72. In addition, remote end 81 of rearward groove leg 77 is located at the rearwardmost axial position of groove 72, while remote end 79 of forward groove leg 75 is positioned about midway between the axial length of groove 72.

Figure 13B:
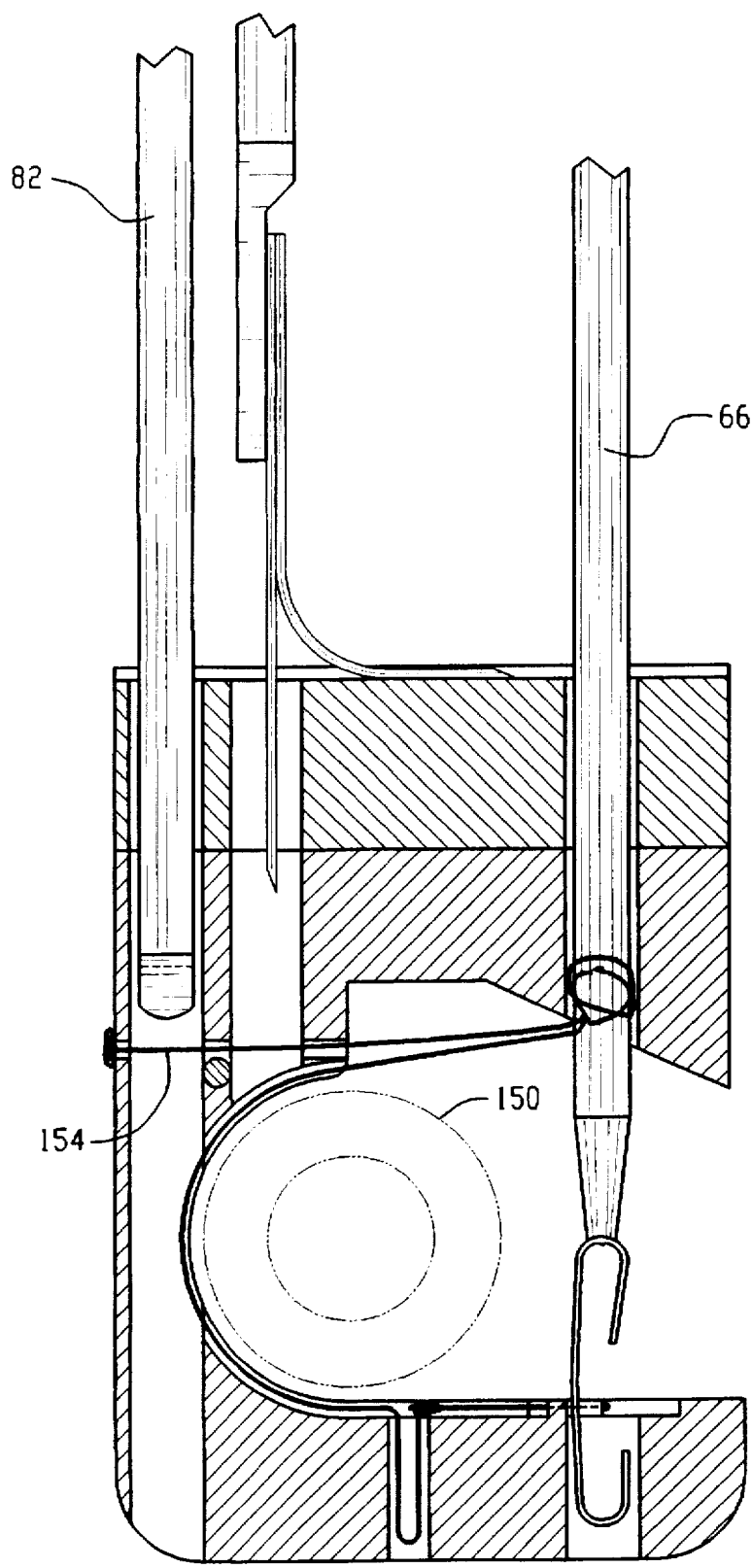
FIG. 13B is a fragmentary cross-sectional view similar to FIG. 13A showing the inventive ligation apparatus in a first stage of activation with the grasping member in a fully extended position.

As more fully discussed below, a pin 76 on hook rod 66 is located in groove 72 for axially moving capture member or hook assembly 19 in instrument 11 of the ligation apparatus. From the configuration of groove 72, it can be seen that with pin 76 initially engaging remote end 79 of forward groove leg 75, capture member 19 will be an initial rest position located axially about midway between its fully extended and fully retracted position. As inner cam 64 is rotated, pin 76 moves capture member 19 from its initial rest position (FIG. 13A) to a fully extended position (FIG. 13B)

when cam 64 rotates about 90° from its initial position as illustrated in FIG. 2. Continued rotation of inner cam 64 through an additional 270° will then cause capture member 19 to then move axially rearward from its fully extended position to its fully retracted position (FIG. 13E) until pin 76 engages remote end 81 of rearward groove leg 77.

Figure 7:
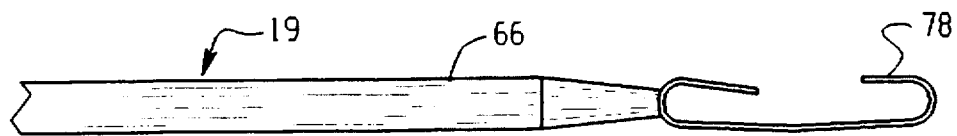
FIG. 7 is fragmentary, axial view of the grasping member of the inventive ligation apparatus.
Figure 8:
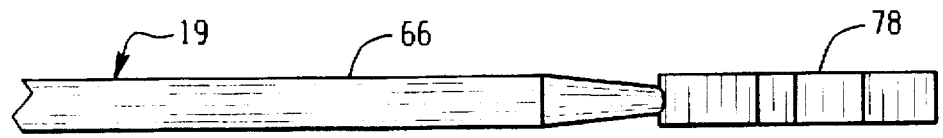
FIG. 8 is a fragmentary, axial top view of the grasping member of FIG. 7.

As shown in FIGS. 7, 8 and 13A, capture member or hook assembly 19 includes grasping member 78 on first end 68 of hook rod 66. Grasping member 78 is provided for capturing the end of a suture material 16, moving the suture material around the vessel or duct 150 to form a knot and for drawing the knot at least partially tight. This is accomplished by moving actuator 42 from its fully open position as shown in FIGS. 1A and 1B to a fully closed position. As a result, outer and inner drive cams 48 and 64 rotate in a clockwise direction, as viewed from the rear, thereby causing the grasping member to move from its initial rest position (FIG. 13A) through successive intermediate positions (FIGS. 13B, 13C and 13D) to its final position (FIGS. 13E), as discussed above.

With reference now to FIGS. 1B, 13A, 11 and 12, tightening means 20 for tightening the ligature knot comprises push assembly 23 and a tightening member which comprises a second or push rod 82. Push rod 82 extends from a first end 84 to a second end 86 and includes a recess 90 on front end 84 (FIGS. 11 and 12) and a bearing surface 101 on second end 86 (FIG. 1B). Push assembly 23 comprises front drive cam 80 having a front end surface 88 and a back end surface 90 fixedly secured to a disk 92.

Front end surface 88 of front drive cam 80 faces the front of ligating apparatus 10 and is composed of two sections, a flat section 97 and a sloped or helical section 99. Flat section 97 and helical section 99 each extend approximately 180° in angular displacement. In addition, the two sections are arranged so that bearing surface 101 of push rod 82 rides on flat section 97 during the first 180° or so of rotation and then rides on helical section 99 during the second 180° or so of rotation. With this configuration, push rod 82 of the tightening means 20 remains in place in its fully retracted position during the first half or so of the actuation cycle of the inventive ligation apparatus. Thereafter, push rod 82 moves axially forward from its fully retracted position (FIGS. 1B, 13A, 13B and 13C) to its fully extended position. (FIG. 13E).

To keep rod 82 in contact with front surface 88 of front drive cam 80, biasing means such as tension spring 93 are positioned between frame 12 and a pin 94 extending from push rod 82. As shown in FIG. 1B, pin 94 extends through a longitudinal slot 96 having a predetermined length. As pin 94 rides in slot 96, axial displacement of push rod 80 is limited by the length of slot 96.

Figure 3A:
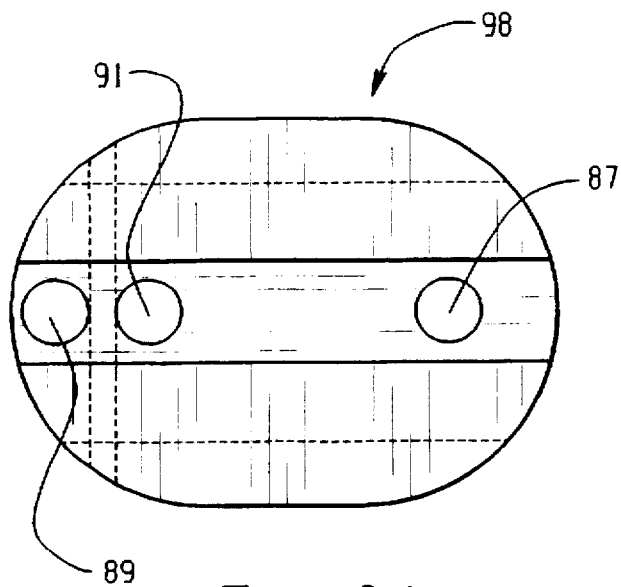
FIG. 3A is an enlarged view taken on line 3—3 of FIG. 1A and showing an inside surface of the front end section of the instrument of the inventive ligation apparatus.
Figure 3B:
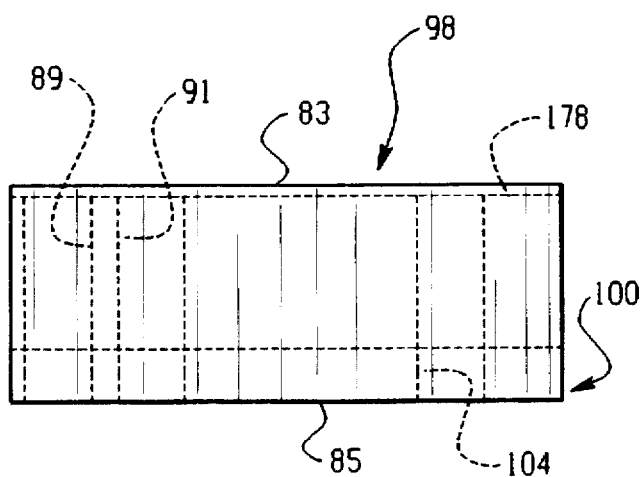
FIG. 3B is a side view of the front end section illustrated in FIG. 3A.
Figure 3C:
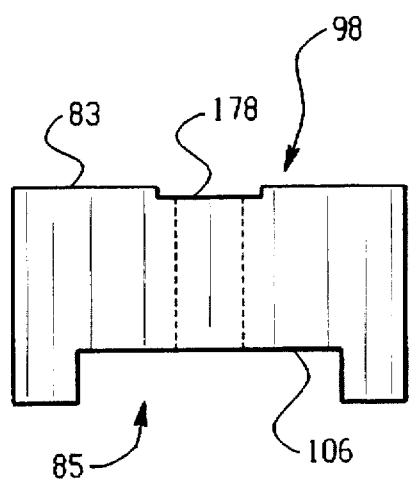
FIG. 3C is an end view of the front end section illustrated in FIG. 3A.
Figure 4A:
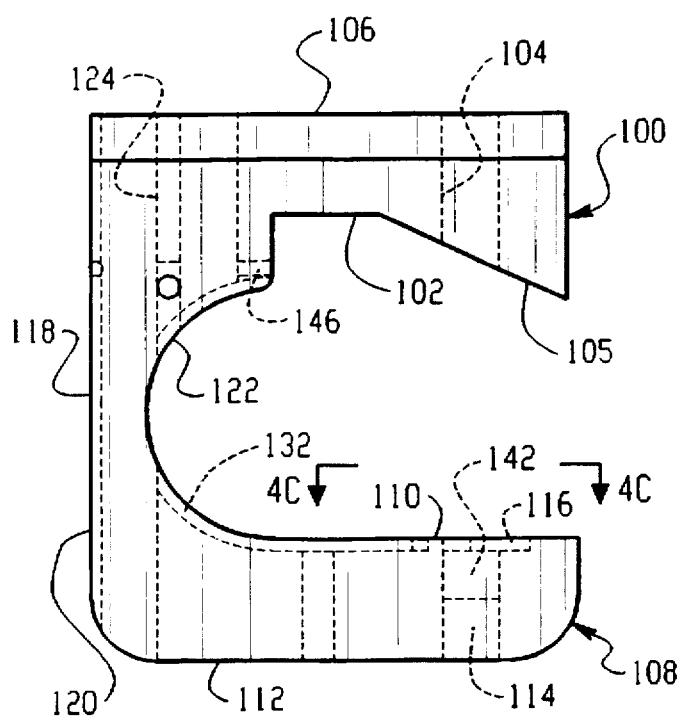
FIG. 4A is an enlarged side view of the cartridge blank of the present invention, this cartridge blank when loaded with a preformed ligature forming the cartridge illustrated in FIGS. 1A and 1B.
Figure 4B:
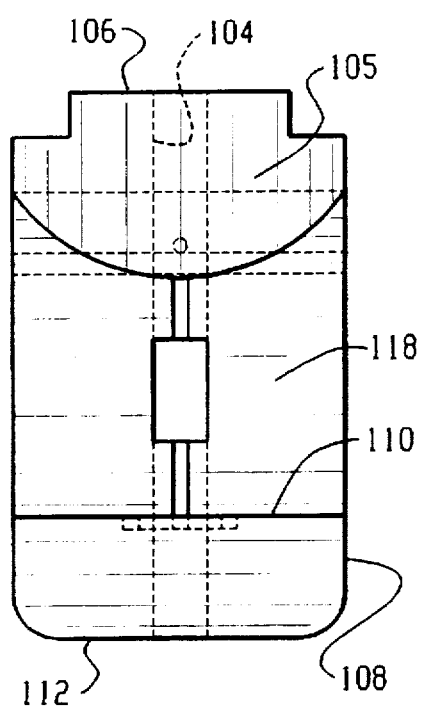
FIG. 4B is an enlarged front view of the cartridge blank of FIG. 4A.
Figure 4C:
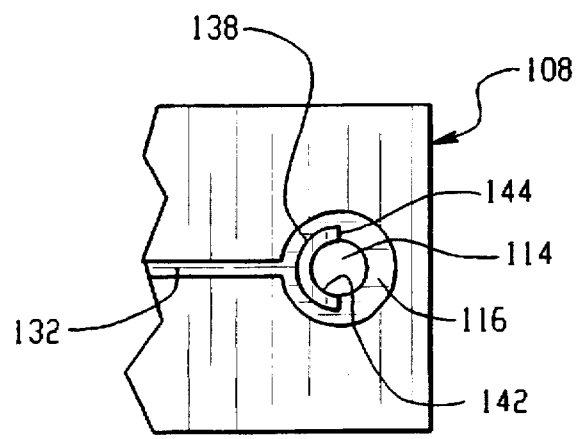
FIG. 4C is an enlarged top view of the cartridge blank taken along line C—C of FIG. 4A.

In their extended positions, capture member 19 and tightening member 82 extend into cartridge 14 for forming and tightening a ligature knot therein. In order to guide these members in proper position, the instrument 11 of the inventive ligation apparatus includes a front end 98, which is illustrated in FIGS. 3A, 3B and 3C. Front end 98 is composed of a solid piece of material having an interior face 83 and an exterior face 85 for releasable attachment to cartridge 14, as discussed below. Front end 98 defines a grasping member passageway 87 for receiving grasping member 78 and hook rod 66 of instrument 11 as well as a push rod passageway 89 for receiving push rod 82 of instrument 11. In addition, front end 98 also defines a cutting rod passageway 91, whose function will be explained later, while the interior face 83 of front end 98 defines a slot 178, whose function will also be explained later.

With reference to FIGS. 4A, 4B, 4C, 5 and 6, cartridge 14 is removably attached to exterior face 85 of front end 98 of instrument 11 of ligation apparatus 10 by means (not shown). For this purpose any attachment system, mechanism or assembly which will allow cartridge 14 to be releasably attached to front end 98 and replaced with another cartridge can be used. Examples of such systems, mechanisms and assemblies are screws, bolts, adhesive, snap-fittings, strings, wires, press-fittings, slide-fittings and so forth.

Figure 5:
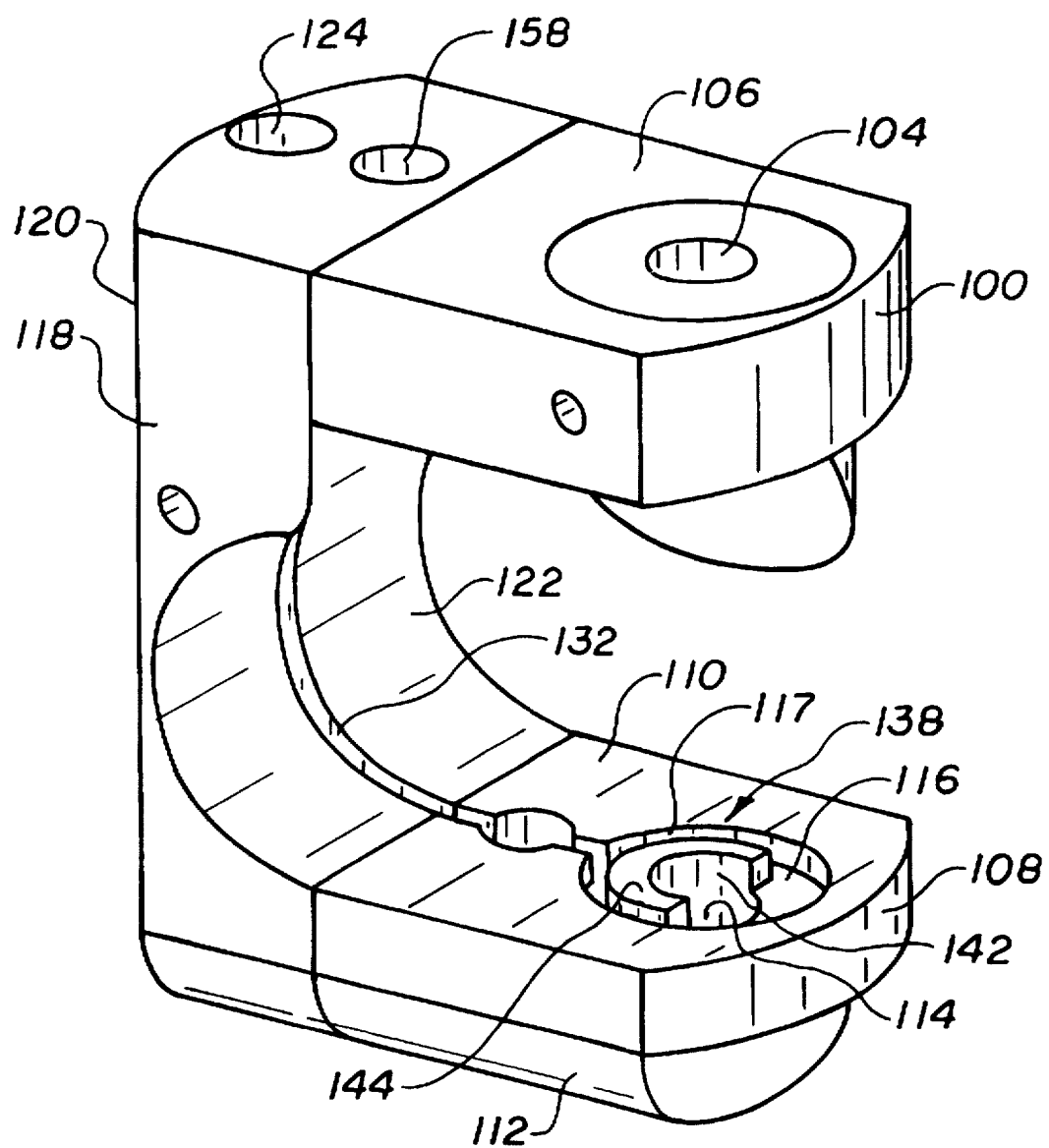
FIG. 5 is a perspective view of the cartridge blank of FIGS. 4A, 4B and 4C.
Figure 6:
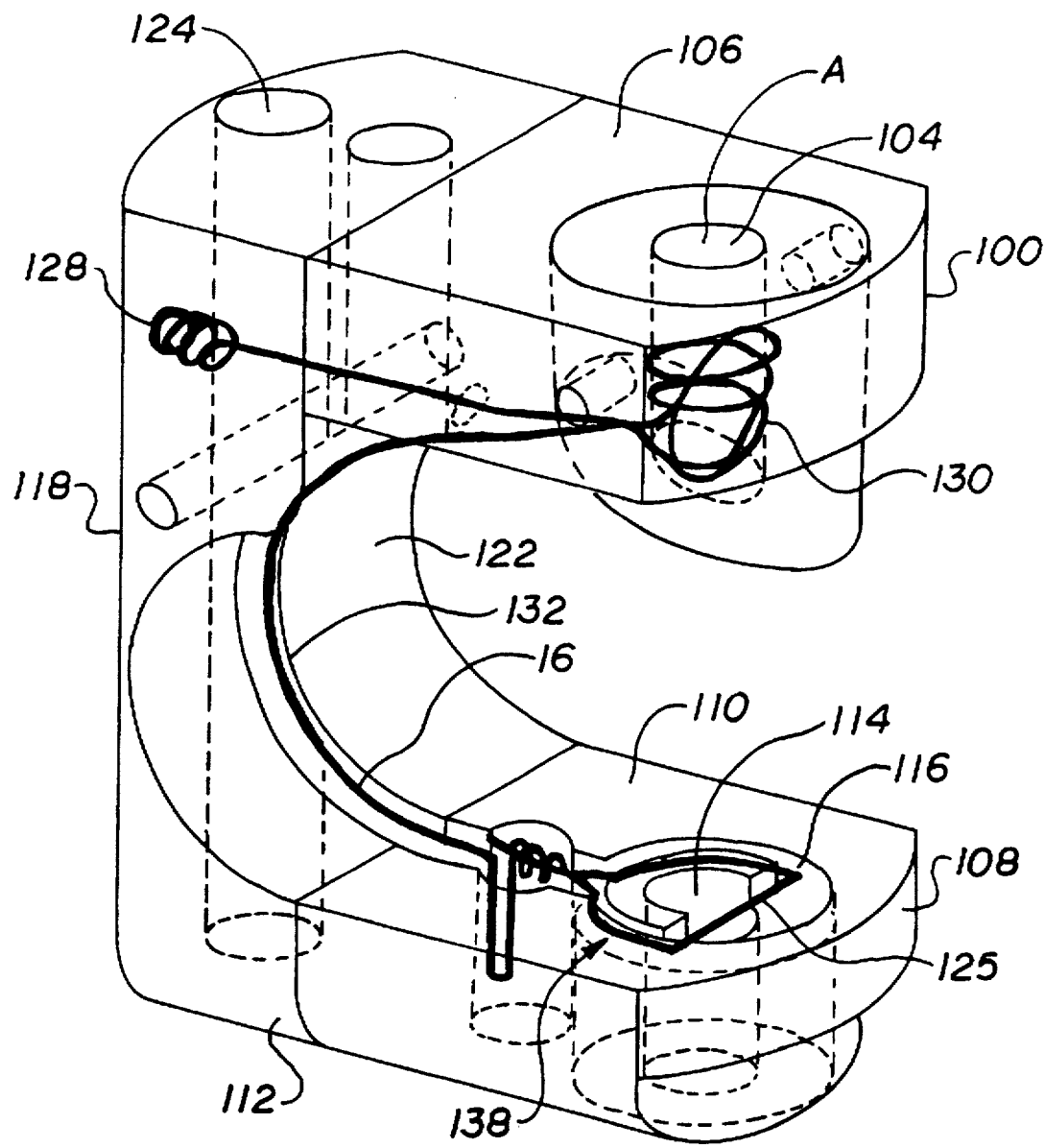
FIG. 6 is a view similar to FIG. 5 showing a completed cartridge of the present invention comprising the cartridge blank of FIGS. 4A, 4B, 4C and 5 loaded with a length of suture material in the form of a preformed ligature.

As illustrated particularly in FIGS. 5, 6 and 13A, cartridge 14 is configured and dimensioned to retain a pre-formed piece of suture material 16 and to envelop a blood vessel or bodily duct 150 therein. In a preferred embodiment of the invention, the cartridge 14 is composed of a C-shaped body member and has a first end section or proximal arm 100 that is removably attached to exterior surface 85 of front end 98 of instrument 11. First end section 100 has an inner surface 102 and a grasping member guide comprising an aperture 104 extending axially therethrough. Inner surface 102 of first end section 100 has a region 105 about aperture 104 that extends at an oblique angle to further envelop a portion of the blood vessel placed in the cartridge. First end section 100 also has an outer surface 106 for mating engagement with exterior surface 85 of front end 98 of instrument 11.

Cartridge 14 also has a second end section or distal arm 108 which has an inner surface 110 opposing inner surface 102 of first end section 100, an outer surface 112 and a cavity 114. Cavity 114 has an opening 116 defined by inner surface 110, the purpose of which will be described below.

A base section 118 of cartridge 14 is integral with first end section 100 and second end section 108. Base section 118 has an outer surface 120 and an inner surface 122 contiguous with inner surfaces 102, 110 of first and second end sections 100, 108, respectively. A tightening bore 124, whose function will be described below, extends axially through base section 118 from outer surface 106 to outer surface 112 of the cartridge. As shown in FIG. 13A, the remote ends of proximal and distal arms 100 and 108 extend past vessel or duct 150 when contained in the C-shaped opening of cartridge 14.

With reference to FIGS. 6 and 13A, a piece of suture material 16 is positioned in cartridge 14. Suture material 16 includes a first end 126 defining a noose 125 therein, a second end 128, and a plurality of loops 130 located in grasping member aperture 104 between first and second ends 126, 128. A channel 132 is formed in contiguous inner surfaces 102, 110, 122 of first end section 100, second end section 108 base section 118, respectively. Channel 132 releasably retains the piece of the suture material 16 between loops 130 and noose 125 around blood vessel 150.

To releasably retain loops 130 in grasping member aperture 104, aperture 104 has a diameter larger than the diameter of hook rod 66 and grasping member 78. Loops 130 are held within grasping member aperture 104 by an adhesive material A such as a wax or paraffin coating which adheres the loops to the inner surface of the aperture. See FIG. 6. It should be understood that other conventional means for adhering the loops 130 may be used such as press fitting the loops for a mold fit.

With reference to FIGS. 5, 6 and 13A to C, a noose holder 138 and securing station 140 are positioned in cartridge 14 to releasably hold the two ends 126, 128 of suture material 16 within cartridge 14. Noose holder 138 comprises a C-shaped region 144 seated in opening 116 of the cavity 114 in second end section 108 of cartridge 14. The "inside" surface of C-shaped noose holder 138 is defined by a bore 142 comprising an extension of cavity 114 in second end section 108 of the cartridge, while the "outside" surface of C-shaped noose holder 138 is spaced from the outer periphery of opening 116 to allow space 117 for receiving a length of suture material. Releasable adhesive such as a paraffin or other wax may be deposited on the outside C-surface of C-shaped noose-holder 138 to releasably hold noose 125 in a stirrup-like configuration with a portion of noose 125 spanning a diameter of bore 142.

Securing station 140 is provided in cartridge 14 for holding the second end of suture material 16. Securing station 140 comprises an aperture 146 positioned through base section 118 from the outer surface 120 across tightening bore 124 and through to inner surface 122. The portion of suture material 16 from loops 130 to second end 128 is positioned through aperture 146 with second end 128 of the suture material being positioned through aperture 146 in outer surface 120 of base 118 and tied at a tip end 148. Tip end 148 has a diameter larger than the diameter of the aperture 146 so as to be retained beyond the surface 120 of base section 118. Tip end 148 may be formed by any conventional means known in the art which retains one end of a string or thread-like material positioned through an aperture such as a knot located outside the aperture and having a diameter larger than the diameter of the aperture.

To operate ligation apparatus 10, cartridge 14 preloaded with suture material 16 in the form of a pre-formed ligature, is attached to the front end 98 of the instrument 11. Ligature apparatus 10 is then positioned such that the inner surfaces 102, 110 and 122 of cartridge 14 envelop a vessel or duct 150 to be ligated. With cartridge 14 in this position, suture material 16, from first end 126 to the loops 130, also surrounds vessel 150, and the apparatus is ready for activation to thereby automatically form a completed ligature.

Activation of ligature apparatus 10 is initiated by moving actuator 42 towards handle 26. This initiates forward movement of link bar 46 in instrument 11, which in turn rotates outer drive cam 48 via pin 54. As outer drive cam 48 rotates, inner drive cam 64 positioned within and integral with outer cam 48 also rotates. During the first 90° or so of rotation, inner cam pin 76 on hook rod 66 rides in forward groove leg 75 of inner cam groove 72. As this occurs, hook rod 66 and grasping member 78 move from an initial rest position as illustrated in FIG. 13A to a fully extended position, as illustrated in FIG. 13B. As can be seen from these figures, grasping member 78 extends through grasping aperture 104 of the first end section 100 of cartridge 14 and also through suture loops 130 in grasping aperture 104 into full engagement with cavity 114 in second end section 108 of cartridge 14.

As inner and outer drive cams 64 and 48 continue rotating past 90° from their initial position, pin 76 on hook rod 66 engages rearward groove leg 77 of inner drive cam 64. Continued rotation of the drive cams causes hook rod 66 and hence grasping member 19 to move rearwardly from their fully extended position as shown in FIG. 13B to their fully retracted position as shown in FIG. 13E.

Figure 13C:
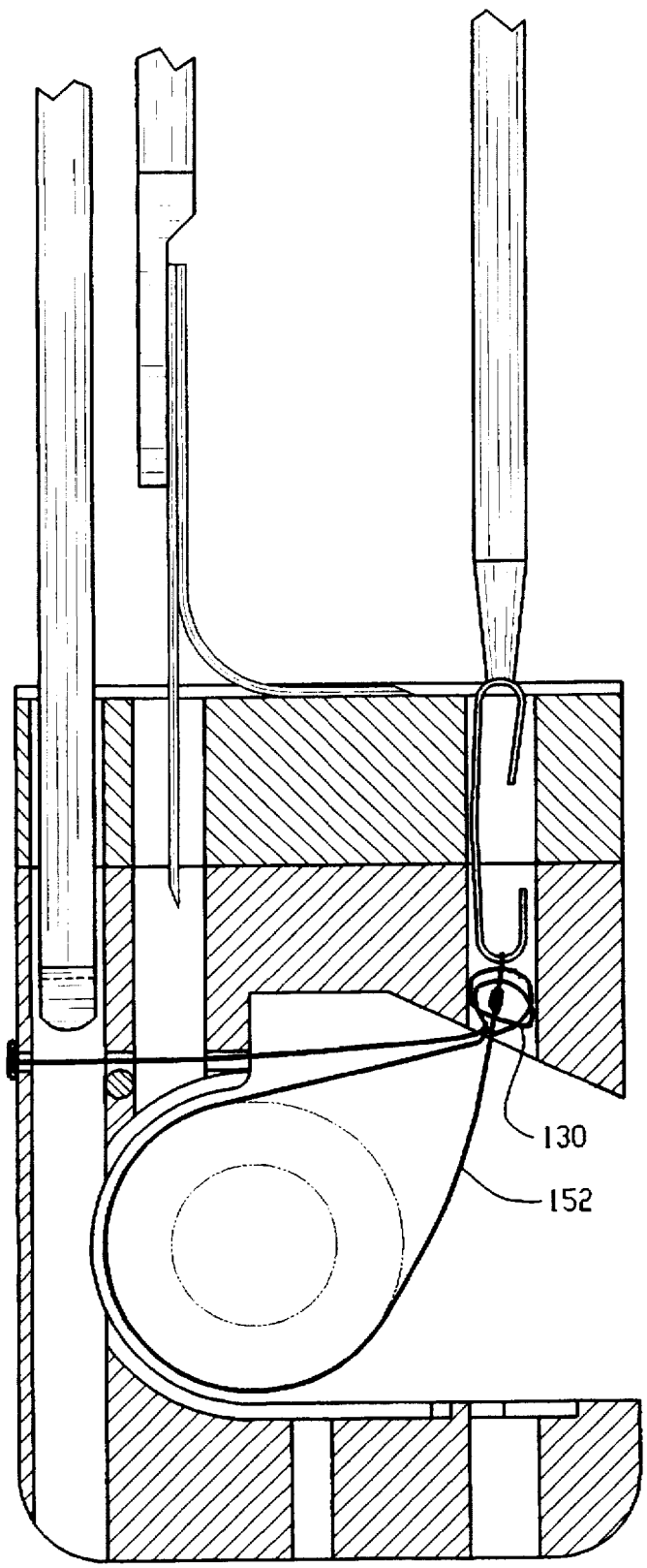
FIG. 13C is a fragmentary cross-sectional view similar to FIG. A showing the inventive apparatus in an intermediate configuration in which the grasping member has pulled one end of the suture material contained in the suture cartridge through loops formed in the other end of the suture material for forming a ligature knot.
Figure 13D:
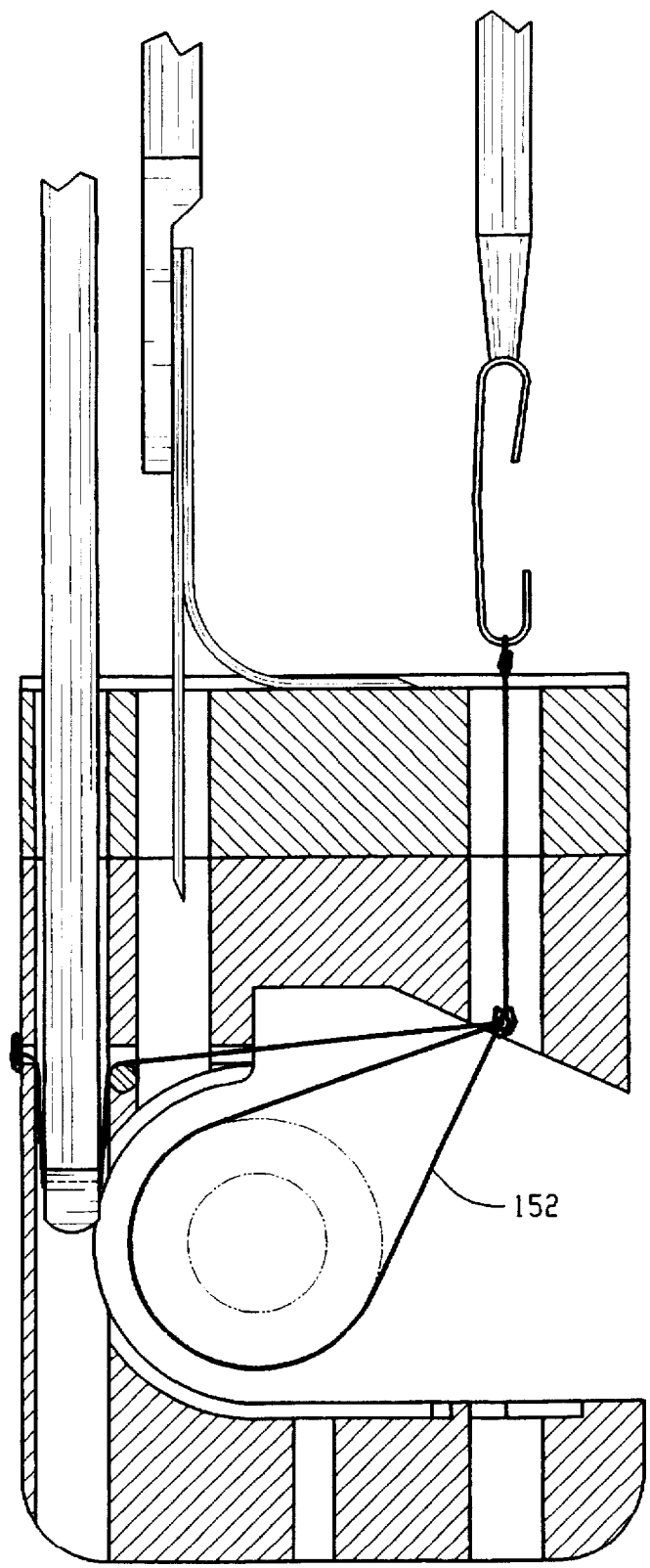
FIG. 13D is a fragmentary cross-sectional view similar to FIG. 13A in which the inventive apparatus is in a later intermediate configuration in which the grasping member and the tightening member of the inventive ligature apparatus have substantially drawn both ends of the suture material so that the ligature knot is in a substantially, but not completely, tightened condition.
Figure 13E:
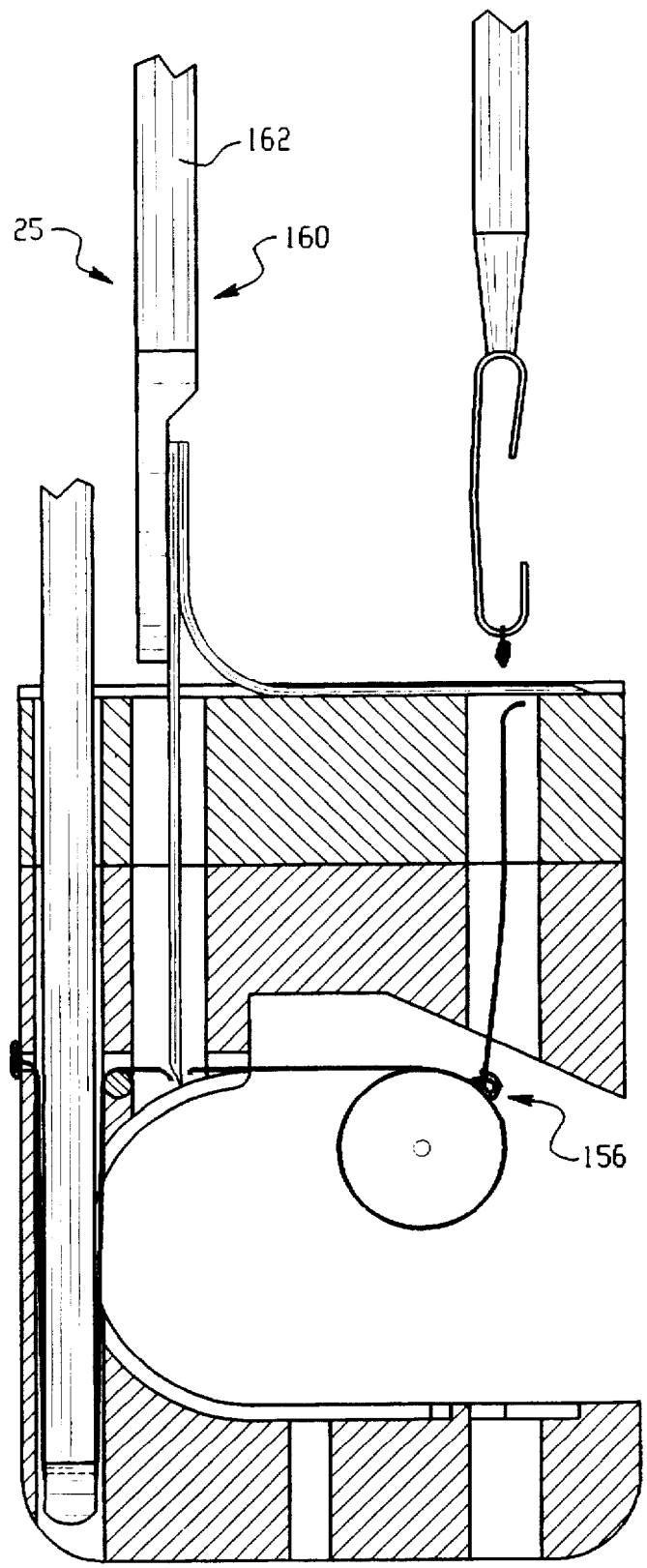
FIG. 13E is a cross-sectional view similar to FIG. 13A in which the inventive ligature apparatus is in a final configuration in which the grasping and tightening member have drawn both ends of the suture material to a completely tightened position to form a completed ligature knot and further in which the ends of the suture material have been cut to free the completed ligature from the remainder of the inventive ligation apparatus.

Referring to FIGS. 13B, 13C, 13D and 13E, as grasping member 78 retracts, the portion of noose 125 positioned across the diameter of bore 142 of C-shaped noose-holder 138 is hooked by grasping member 78. As grasping member 78 continues to retract, grasping member 78 pulls noose 125 and the immediately trailing portion of suture material 16 around vessel 150 and through aperture 104 and loops 130. As this occurs, the portion of suture material held in channel 132 is released therefrom thereby bringing a portion of suture material 16 into immediate contact with vessel 150. Grasping member 78 thus forms and partially tightens a suture loop 152 around vessel 150. Continued movement of actuator 42 to a fully closed position causes grasping member 78 to move to a fully retracted position as illustrated in FIG. 13E, thereby pulling first end 126 of suture material 16 to a fully tightened position. As shown in FIGS. 13C, 13D and 13E, when grasping member 78 moves past loops 130 to its fully retracted position of FIGS. 13E, tightening or push assembly 20 is also actuated to further tighten suture loop 152. When the drive cam assembly, i.e. inner drive cam 48, outer drive cam 64 and front drive cam 80, moves through its first 180° or so of rotation for actuating grasping member 78 as illustrated in FIGS. 13A, 13B and 13C, push rod 82 remains in its fully retracted position. This is because bearing surface 101 of second end 86 of the push rod rides on flat section 97 of front end surface 88 of drive cam 64. However, when the cam assembly rotates through its second 180° or so of travel, bearing surface 101 engages helical section 99 of front end surface 88. This causes push rod 82 to move axially forward, which in turn causes recess 90 on the front end 94 of push rod 82 to extend into bore 124 and engage the portion 154 of suture material 16 positioned across the diameter of bore 124. See FIG. 13D. As push rod 82 further extends into bore 124, portion 154 of suture material is further pushed into bore 124 to draw this end of the suture loop 152 tight. The action of push rod 82 extending all the way into bore 124 in cooperation with grasping member 78 moving to its fully retracted position pulls suture material 16 completely tight as illustrated in FIG. 13E, thereby forming a completed ligature knot 156.

Figure 9:
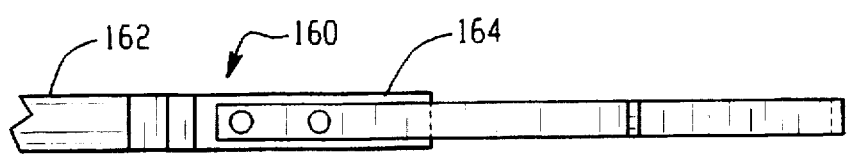
FIG. 9 is a fragmentary top view of the cutting mechanism of the inventive ligation apparatus.
Figure 10:
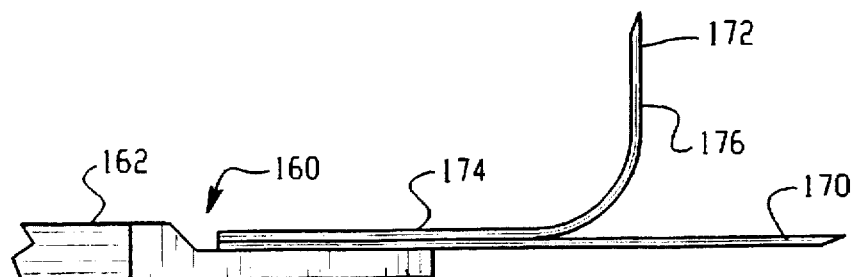
FIG. 10 is a fragmentary, axial side view of the cutting mechanism of FIG. 9.
Figure 11:
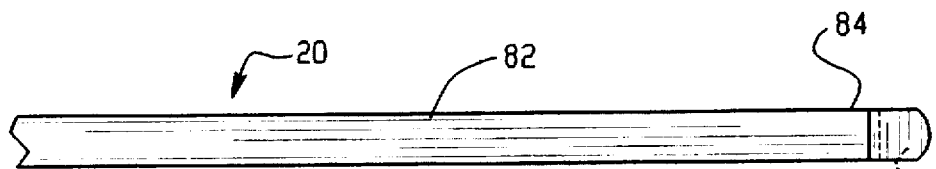
FIG. 11 is a fragmentary, axial top view of the pushing assembly of the inventive ligation apparatus.
Figure 12:
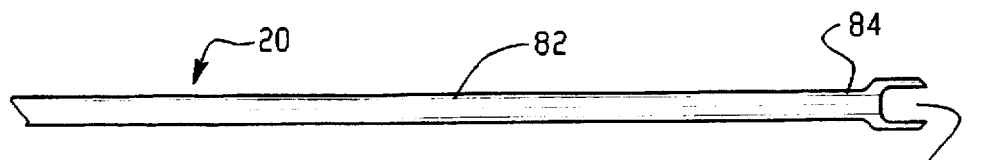
FIG. 12 is a fragmentary, axial side view of pushing assembly of FIG. 11.

In a preferred embodiment of the invention, a cutting assembly is also provided in the inventive ligature apparatus for cutting the completed ligature from excess suture material in cartridge 14. In this embodiment, as shown in FIGS. 4A, 4B, 4C, 5 and 6, cartridge 14 also includes a cutting bore 158 positioned between and substantially parallel to tightening bore 124 and grasping member aperture 104 of first end section 100 of the cartridge. As seen in FIGS. 9, 10 and 13E, cutting of suture material 16 is accomplished by a cut assembly 25 which includes a cutting mechanism 160 configured to cut suture material 16 between second end 128 and loops 130 and also between loops 130 and noose 126.

In a particularly preferred embodiment, cutting mechanism 160 is composed of a cutting member or rod 162 extending axially from a first end 164 to a second end 166 (FIG. 1A) and a trigger mechanism for extending cut rod 162 from a retracted position to an extended cutting position. Trigger mechanism 160 includes a trigger 168, a link 182 connecting trigger 168 and cutting rod 162 and a tension spring 190 biasing cutting rod 162 in its retracted position. A first cutting blade 170 is connected to a first end 164 of cutting rod 162 and extends in substantial alignment from first end 164 into the cutting bore 158 of cartridge 14. A second cutting blade 172 is positioned adjacent first cutting blade 170 and is connected to first blade 170 and first end 164 of cutting rod 162. Cutting blades 170, 172 can be connected to first end 164 by any conventional connector such as screw type fasteners. Second cutting blade 172 has an arcuate L-shaped configuration with a first portion 174 substantially parallel to first cutting blade 170, and a second portion 176 substantially perpendicular the first portion 170. Second portion 176 is positioned in slot 178 arranged in interior face 83 of front end 98 of body 12 of the ligation apparatus.

When actuated by the trigger mechanism 168, cutting rod 162 moves to an extended position and first cutting blade 170 extends into cutting bore 158 to engage and sever the portion of the suture material 16 across bore 158. Concurrently, second blade 172 extends through slot 178 and across aperture 104 thereby engaging and severing the portion of suture material 16 extending across this aperture. When the cutting operation is over, release of trigger 168 allows tension spring 190 to draw cutting rod 162 and hence cutting blades 170 and 172 back into a retracted position.

Once the cutting operation is over, ligation device 10 may be removed from the patient. Upon return of hook rod 66, push rod 82 and cut rod 162 to their initial positions, which occurs through movement of actuator 42 from its fully closed to its fully open position, empty cartridge 14 can be readily replaced with another cartridge preloaded with a preformed piece of suture material. Once the new cartridge is in place, ligation apparatus can be used again to form another ligature knot.

It will thus be appreciated that the inventive ligation apparatus enables multiple ligations to be preformed in rapid succession using the same instrument for each operation. This considerably reduces expense, since it eliminates the need for a new instrument to be used for each ligation. In addition, it contributes significantly to a safer surgical procedure, since successive ligations can be performed rapidly, thereby reducing the over-all time needed for the procedure. These benefits are particularly significant in laparoscopy, where access to the surgical site is limited and operational ease and convenience are desirable.

The invention has been described with reference to a preferred embodiment and certain alternatives. Obviously, modifications and alterations will occur to others upon reading and understanding the preceding detailed specification. For example, cutting mechanism 160 instead of including a separate trigger mechanism as described above can be connected to push rod 82 so that cutting blades 170 and 172 are brought into engagement with suture material 116 as it is tightened by the push rod and grasping member 78. It is intended that the invention be construed as including all such alterations and modifications insofar as they come within the scope of the appended claims or the equivalents thereof.

What is claimed is:

1. A reusable ligation assembly for use in ligating a vessel or duct, said ligation assembly comprising:

an elongated frame;

a holding member for receiving the vessel or duct therein, said holding member releasably secured to said frame and carrying a length of suture material having a noose formed on a first end, a second end and at least one loop therebetween, said holding member having
   (a) means for retaining a piece of suture material around a portion of the vessel or duct when the vessel or duct is placed therein,
   (b) means for releasably retaining said noose,
   (c) means for releasably retaining said at least one loop, and
   (d) means for securing the second end of the suture material;

capture means for moving said noose around the blood vessel and through said at least one loop to form a knot and connected to and extendable from said elongated frame member;

tightening means for tightening the suture material around the blood vessel and connected to and extendable from said elongated frame member; and cutting means incorporated within and extendable from said elongated frame member for cutting the suture material intermediate the ends of the suture material and the knot.

2. The ligation assembly of claim 1 wherein the means for securing the second end of the suture material comprises an aperture positioned through the base section with the second end of the suture material positioned therethrough, the second end of the suture material having a tip end extending beyond the outer surface of the base section with a diameter larger than the diameter of said aperture.

3. The ligation assembly of claim 1 wherein said capture means comprises:

a first rod member extending axially from a first end to second end, said first rod member being partially supported within said elongate frame and axially moveable between extended and retracted positions within said elongate frame;

a capture member disposed on the first end of said first rod member for engaging the noose on the suture material when said first rod member is moved to the extended position and for transferring the noose into engagement with the loops on the suture material when said first rod member is moved to a retracted position;

first actuating means comprising a handle and an actuator pivotally connected to said handle, said actuating means responsive to the manipulation of said actuator for moving said first rod member between extended and retracted positions;

wherein movement of said first rod member from extended to retracted position transfers the noose into engagement with the loops to form a ligation loop around the blood vessel and to form a knot.

4. The ligation assembly of claim 1, wherein the means for cutting the suture material intermediate the ends of the suture material and the knot comprises:

a cutting mechanism configured to cut the suture material between the second end and the loops and also between the loops and the noose after the knot is tightened by said tightening means and said capture means.

5. A reusable ligation assembly for use in ligating a vessel or duct, said ligation assembly comprising:

an elongated frame;

a C-shaped holding member for receiving the vessel or duct therein comprising a first end section removably attachable to said elongated frame having an outer surface adjacent said holding member, an inner surface, and an aperture extending transversely therethrough;

a second end section having an inner surface opposing the inner surface of said first end section, an outer surface, and a cavity with an opening defined by the inner surface of said second end section;

a base section integral with said first end section and said second end section and having an outer surface and an inner surface contiguous with the inner surfaces of said first end section and said second end section, and a longitudinal bore extending transversely therethrough, said holding member releasably secured to said frame and carrying a length of suture material having a noose formed on a first end, a second end and at least one loop therebetween, said holding member having
   (a) means for retaining a piece of suture material around a portion of the vessel or duct when the vessel or duct is placed therein,
   (b) means for releasably retaining said noose,
   (c) means for releasably retaining said at least one loop, and
   (d) means for securing the second end of the suture material;

capture means for moving said noose around the blood vessel and through said at least one loop to form a knot and connected to and extendable from said elongated frame;

tightening means for tightening the suture material around the blood vessel and connected to and extendable from said elongated frame; and cutting means incorporated within and extendable from said elongated frame for cutting the suture material intermediate the ends of the suture material and the knot.

6. The ligation assembly of claim 5, wherein the means for retaining a piece of suture material around a portion of the blood vessel comprises a channel positioned along the inner surfaces of said first end section, said base section and said second end section for releasably holding the suture material between the loops and the noose in the suture material and around a portion of the blood vessel when the blood vessel is placed therein.

7. The ligation assembly of claim 5, wherein the means for releasably retaining at least one loop intermediate the noose and the second end of the suture material comprises a loop holder disposed within the aperture of said first end section, said loop holder having a bore, a loop holder region defining the bore, and a retaining means to releasably hold at least one loop in the suture material around the bore.

8. The ligation assembly of claim 7 wherein said loop holder comprises a cylinder having a first end surface extending at an oblique angle from the inner surface of the first end section to further envelop a portion of the blood vessel.

9. The ligation assembly of claim 5, wherein the means for releasably retaining a noose at one end of the suture material comprises a noose holder seated in the cavity of said second end section having a bore and a region surrounding said bore configured to releasably hold the noose around a portion of the bore.

10. The ligation assembly of claim 9 wherein said noose holder further comprises a C-shaped member surrounding the opening of the bore of said noose holder for press fitting the noose into a resilient stirrup configuration.

11. The ligation assembly of claim 9, wherein said noose holder comprises a paraffin coated C-shaped member surrounding the opening of the bore of said noose holder for press fitting the noose into a resilient stirrup configuration thereby permitting the grasping member of said first rod to pass through the stirrup when said first rod is moved into the extended position and further permitting the grasping member to retain the noose in the stirrup configuration when said first rod member is retracted.

12. The ligation assembly of claim 5 wherein said capture means comprises:

a first rod member extending axially from a first end to second end, said first rod member being partially supported within said elongate frame and axially moveable between extended and retracted positions within said elongate frame;

a capture member disposed on the first end of said first rod member for engaging the noose on the suture material when said first rod member is moved to the extended position and for transferring the noose into engagement with the loops on the suture material when said first rod member is moved to a retracted position;

first actuating means comprising a handle and an actuator pivotally connected to said handle, said actuating means responsive to the manipulation of said actuator for moving said first rod member between extended and retracted positions;

an outer link bar having a first end and a second end having a outer cam pin extending therefrom;

an outer drive cam rotatably positioned within said elongate frame and having an outer surface, said outer surface having an outer drive cam groove therein, said outer cam pin positioned in said outer drive cam groove such that manipulation of said handle assembly causes said outer cam pin to rotate said outer drive cam;

an inner drive cam movable with said outer drive cam such that rotation of said outer drive cam rotates said inner drive cam, said inner drive cam having an inner drive cam surface, said inner drive cam surface having an inner drive cam groove therein;

a said first rod member having an inner cam pin extending therefrom, said inner pin positioned in said inner drive cam groove such that upon rotation of said inner drive cam the inner cam pin moves through the inner groove axially moving the first rod member from retracted to extended positions; and wherein movement of said first rod member from extended to retracted position transfers the noose into engagement with the loops to form a ligation loop around the blood vessel and to form a knot.

13. The ligation assembly of claim 12 wherein said tightening means comprises:

a second rod member axially extending from a first end to a second end, said second rod member being partially supported within said elongate frame and axially moveable within said frame to an extended position wherein the first end of said second rod member engages a piece of suture material lying between the second end and loops thereof;

a front drive cam having a sloped front end surface and a back end surface, said back end surface fixedly secured to the front end of said outer drive cam, said sloped front end surface having placed thereon the second end of said second rod member such that rotation of said outer drive cam rotates said front drive cam axially moving said second rod member to an extended position;

biasing means for biasing the second end of said second rod member against said front drive cam;

wherein said first actuating means moves said second rod member to the extended position as said first actuating means moves said first rod member from a retracted position to an extended position and back to a retracted position so that said second rod member pushes on the second end of the suture material while said first rod member pulls on the noose thereby tightening the knot in the suture material.

14. The ligation assembly of claim 13, wherein said second rod member is moved into engagement with the suture material as said first rod member transfers the noose into engagement with the loops on the suture material thereby tightening the knot.

15. The ligation assembly of claim 5 wherein said means for cutting the suture material intermediate the ends of the suture material and the knot comprises:

a cutting mechanism configured to cut the suture material between the second end and the loops and also between the loops and the noose after the knot is tightened by said tightening means and said capture means comprising:

a) a third rod member extending axially from a first end to second end, said third rod member being partially supported within said elongated frame and movable into an extended position and back to a retracted position;

b) a first cutter integrally connected to the first end of said third rod member and extending a predetermined distance therefrom such that movement of said third rod member to an extended position moves said first cutter into cutting engagement with the portion of suture material between the second end and the loops of said suture material; and c) a second cutter connected adjacent to said first cutter and to the first end of said third rod member, said second cutter having a geometric configuration such that movement of said third rod member to an extended position moves the second cutter into cutting engagement with the portion of suture material between the noose and the loops of the suture material after the knot is tightened.

16. The ligation assembly of claim 15 wherein said cutting mechanism includes second actuation means for movement of said third rod from a retracted position to an extended position and back to a retracted position.

17. The ligation assembly of claim 16 wherein said second actuation means comprises:

a pin affixed to the second end of said third rod member;

a link member extending axially from a first end to a second end, said link member being partially supported within said elongate frame and having said second end affixed to said pin;

a trigger mechanism pivotally connected to the first end of said link member such that engagement of said trigger extends said third rod member;

a spring disposed between said second end of said third rod member and said elongate frame so as to bias the third rod member from an extended position to a retracted position;

wherein said second actuating means moves said third rod member from a retracted position to an extended position moving the first and second cutters into cutting engagement while said spring biases the third rod member to the retracted position upon cutting.

18. A holding member for retaining a pre-formed length of suture material having a noose found on a first end thereof, a second end and a plurality of loops therebetween and for attachment to an instrument having a suture material grasper comprising:

a first end section having an outer surface and an inner surface and an aperture extending between the inner and outer surfaces, said outer surface of said first end section removably attachable to the instrument;

a loop holder disposed within the aperture of said first end section having a bore dimensioned for receiving the grasper on the instrument and a loop holder region defining the bore and adapted to releasably hold a plurality of loops in the suture material around the bore;

a second end section having an inner surface opposing the inner surface of said first end section, and a cavity extending between the inner and outer surfaces of said second section and in substantial axial alignment with said aperture of said first end section, said cavity having an opening defined by the inner surface of said second end section and dimensioned for receiving the instrument grasper;

a noose holder seated in the first cavity of said second end having a bore with a diameter larger than the grasper for receiving the grasper, and a region defining the bore and configured to releasably hold the noose around a portion of the bore; and a base section integral with said first end and said second end and having an inner surface contiguous with the inner surfaces of said first end and said second end.

19. A holding member for retaining a pre-formed length of suture material having a noose found on a first end thereof, a second end and a plurality of loops therebetween and for attachment to an instrument having a suture material grasper comprising:

a first end section having an outer surface and an inner surface and an aperture extending between the inner and outer surfaces, said outer surface of said first end section removably attachable to the instrument;

a loop holder disposed within the aperture of said first end section having a bore dimensioned to receive the grasper on the instrument and a loop holder region defining the bore and adapted to releasably hold a plurality of loops in the suture material around the bore;

a second end section having an inner surface opposing the inner surface of said first end section, and a cavity extending between the inner and outer surfaces and in substantial axial alignment with said aperture of said first end section, said cavity having an opening defined by the inner surface of said second end section and dimensioned to receive the instrument grasper;

a noose holder seated in the first cavity of said second end having a bore with a diameter larger than the grasper for receiving the grasper, and a region defining the bore and configured to releasably hold the noose around a portion of the bore; and a base section integral with said first end and said second end and having an inner surface contiguous with the inner surfaces of said first end and said second end and having a first longitudinal bore, a second longitudinal bore and an aperture perpendicular to the first and second longitudinal bores of said base member for positioning a portion of the suture material across the diameters of the longitudinal bores.

20. The holding member of claim 19 wherein said holding member has a channel positioned along the inner surfaces of said first end, said second end and said base section for releasably retaining the portion of suture material lying between a plurality of loops and a noose formed in the suture material.

21. The holding member of claim 19 wherein said loop holder comprises a cylinder having a first end surface which extends below the inner surface of said first end at an oblique angle thereto, removing a sutureless holding member from the elongate frame providing for the releasable attachment of another holding member having a piece of preformed suture material therein.

22. The holding member of claim 18 wherein said second end includes a recess with an opening defined by the inner surface of said second end for receiving a portion of the suture material between the noose and the loops.

23. A method for ligating a blood vessel with suture material comprising the steps of:

a) providing an elongated frame having a distal end, a proximal end and tying means disposed therein;

b) providing a holding member having a piece of preformed suture material having a noose end releasably secured to the holding member and a second end secured to the distal end of said holding member with at least one loop intermediate the noose and second end;

c) positioning the holding member in the distal end of the elongated frame;

d) receiving the blood vessel in the holding member intermediate the noose and loop of the suture material with a portion of the suture material around the blood vessel;

e) moving the noose of the suture material around the blood vessel and through the loop intermediate the ends of the suture material to form a knot;

f) tightening the suture material around the blood vessel; and g) cutting the suture material intermediate the ends of the suture material and the knot.

24. The method of claim 23, further comprising the step of:

removing a sutureless holding member from the elongate frame providing for the releasable attachment of another holding member having a piece of preformed suture material therein.

25. The method of claim 23, wherein the moving step includes extending a first rod through the plurality of loops to retain the noose and retracting the first rod retaining the noose through the loops thereby releasing the suture material from the holding member configuration to surround the vessel or duct with the suture material forming a loose knot, and extending a second rod into contact with the portion of suture material between the plurality of loops and second end to tighten the knot.

26. The method of claim 23, wherein the cutting step includes extending a third rod having a distal end with at least one cutting element thereon into cutting engagement with the portions of suture material intermediate the ends and the knot.

27. A cartridge for carrying a preformed ligature, said cartridge to be attached to a surgical delivery instrument thereby forming a ligation apparatus for use in ligating a tissue conduit with said ligature, said cartridge comprising a body member having a proximal arm, a distal arm and a base, said body member defining a C-shaped opening for receiving said tissue conduit such that remote ends of said proximal and distal arms remote from said base protrude past said conduit when said conduit is received in said C-shaped opening, said proximal arm and distal arm having inside surfaces facing said C-shaped opening, the remote end of said distal arm being adapted to hold a first end of said ligature, the remote end of said proximal arm defining a guide adaptable for receiving and allowing the leading end and body of an elongated capture member adapted to move through said guide, the leading end of said elongated capture member being adapted to capture said first ligature end from the remote end of said distal arm, said guide being adaptable for receiving and holding at least one loop formed in said ligature remote from the first ligature end while said elongated capture member moves therethrough, said base adapted to receive an elongated tightening member arranged generally parallel to said elongated capture member, the inside surfaces of said proximal and distal arms being adapted to hold a body portion of said ligature between the first ligature end and said loop while said cartridge is moved into a use position with said tissue conduit being received in said C-shaped opening, said body member being adapted to hold the second end of said ligature so that movement of said tightening member from a retracted position remote from said body member to an engaged position associated with said base causes tension to be placed on said second ligature end for closing said at least one loop and thereby tying a knot in said ligature.

28. The cartridge of claim 27, wherein said body member defines a cutting aperture therein for receiving the leading end of an elongated cutting member, said cutting aperture arranged so that the leading end of a severing member can sever said ligature between said at least one loop and the second ligature end.

29. The cartridge of claim 28, wherein said proximal arm has an outside surface adapted to be releasably attached to said surgical instrument.

30. The cartridge of claim 27, wherein said proximal arm has an outside surface adapted to be releasably attached to said surgical instrument.

31. A cartridge to be attached to a surgical delivery instrument thereby forming a ligation apparatus for use in ligating a tissue conduit, said cartridge comprising a cartridge and a preformed ligature in said cartridge, said cartridge comprising a body member having a proximal arm, a distal arm and a base, said body member defining a C-shaped opening for receiving said tissue conduit such that remote ends of said proximal and distal arms remote from said base protrude past said conduit when said conduit is received in said C-shaped opening, said proximal arm and distal arm having inside surfaces facing said C-shaped opening, the remote end of said distal arm holding a first end of said ligature, the remote end of said proximal arm defining a guide for receiving the leading end and body of an elongated capture member and allowing the capture member to move through said guide with the leading end of said elongated capture member being adapted to capture said first ligature end from the remote end of said distal arm, said guide receiving and holding at least one loop formed in said ligature remote from the first ligature end such that said loop remains in place in said guide while said elongated capture member moves therethrough.

said base adapted to receive an elongated tightening member arranged generally parallel to said elongated capture member, the inside surfaces of said proximal and distal arms holding a body portion of said ligature between the first ligature end and said loops such that said body portion remains in place while said cartridge is moved into a use position with said tissue conduit being received in said C-shaped opening, said body member holding the second end of said ligature so that movement of said tightening member from a retracted position remote from said body member to an engaged position associated with said base causes tension to be placed on said second ligature end for closing said at least one loop and thereby tying a knot in said ligature.

32. A cartridge to be attached to a surgical delivery instrument thereby forming a ligation apparatus for use in ligating a tissue conduit, said cartridge comprising a cartridge and a preformed ligature in said cartridge, said cartridge comprising a body member having a proximal arm and a distal arm, said body member defining a C-shaped opening for receiving said tissue conduit, said proximal arm and distal arm holding said ligature while said cartridge is moved into a use position with said tissue conduit being received in said C-shaped opening, said proximal arm being adapted to be releasably attached to said surgical instrument.

33. A surgical delivery instrument for use in ligating a tissue conduit, said delivery instrument to be releasably attached to a suture cartridge carrying a preformed ligature, said surgical delivery instrument and said cartridge together forming a ligation apparatus, said cartridge comprising a body member defining a C-shaped opening for receiving said tissue conduit, said body member being adapted to hold said ligature in said C-shaped opening while said cartridge is moved by said instrument into a use position with said tissue conduit being received in said C-shaped opening, said surgical delivery instrument comprising an elongated frame, a front end for releasably mounting said cartridge on said frame, an elongated capture member in said frame, said capture member having a leading end adapted to capture a first end of said ligature held by said cartridge, and an actuator attached to said frame, said actuator adapted to move said capture member from an initial position to an engaged position in which said leading end captures said first ligature end and then to a retracted position, the leading end of said capture member being adapted to hold said first ligature end while said capture member moves from said engaged position to said retracted position so that said preformed ligature is pulled tight around said tissue conduit as said capture member moves back to its retracted position.

34. A surgical delivery instrument for use in ligating a tissue conduit, said delivery instrument to be releasably attached to a suture cartridge carrying a preformed ligature, said surgical delivery instrument and said cartridge together forming a ligation apparatus, said cartridge comprising a body member defining a C-shaped opening for receiving said tissue conduit, said body member being adapted to hold said ligature in said C-shaped opening while said cartridge is moved by said instrument into a use position with said tissue conduit being received in said C-shaped opening, said surgical delivery instrument comprising an elongated frame, a front end for releasably mounting said cartridge on said frame, an elongated capture member in said frame, said capture member having a leading end adapted to capture a first end of said ligature held by said cartridge, and an actuator attached to said frame, said actuator adapted to move said capture member from an initial position to an engaged position in which said leading end captures said first ligature end and then to a retracted position, the leading end of said capture member being adapted to hold said first ligature end while said capture member moves from said engaged position to said retracted position so that said preformed ligature is pulled tight around said tissue conduit as said capture member moves back to its retracted position; and an elongated tightening member in said frame, said tightening member being movable from a retracted position to an engaged position associated with said cartridge, said tightening member engaging said ligature near the second end of said ligature when said tightening member is in said engaged position to thereby cause tension to be placed on said second ligature end for helping pull said ligature tight.

35. The surgical delivery instrument of claim 34, further comprising an elongated severing member in said frame, said severing member being movable from a retracted position to a severing position in which said severing member severs said ligature to thereby release said ligature from said cartridge.

* * * * *